United States Patent [19]

Cawse et al.

[11] Patent Number: 4,652,685
[45] Date of Patent: Mar. 24, 1987

[54] HYDROGENATION OF LACTONES TO GLYCOLS

[75] Inventors: James N. Cawse; Norman E. Johnson, both of Pittsfield; Michael T. Whitaker, Dalton, all of Mass.

[73] Assignee: General Electric Company, Pittsfield, Mass.

[21] Appl. No.: 798,498

[22] Filed: Nov. 15, 1985

[51] Int. Cl.⁴ .................... C07C 29/136; C07C 31/20
[52] U.S. Cl. .................................. 568/864; 549/508; 568/885
[58] Field of Search ............................. 568/864, 885

[56] References Cited

U.S. PATENT DOCUMENTS

| | | | |
|---|---|---|---|
| 4,048,196 | 9/1977 | Brocker et al. | 260/346.11 |
| 4,112,245 | 9/1978 | Zehner et al. | 568/864 |
| 4,301,077 | 11/1981 | Pesa et al. | 260/346.11 |

FOREIGN PATENT DOCUMENTS

| | | | |
|---|---|---|---|
| 60787 | 9/1982 | European Pat. Off. | 568/864 |
| 143634 | 6/1985 | European Pat. Off. | 568/864 |
| WO82/03854 | 11/1982 | PCT Int'l Appl. . | |
| 575380 | 2/1946 | United Kingdom | 568/864 |
| 1230276 | 4/1971 | United Kingdom . | |
| 1314126 | 4/1973 | United Kingdom . | |
| 1344557 | 1/1974 | United Kingdom . | |
| 1512751 | 6/1978 | United Kingdom . | |

Primary Examiner—J. E. Evans
Attorney, Agent, or Firm—Richard J. Traverso; William F. Mufatti; Edward K. Welch, II

[57] ABSTRACT

Lactones, particularly gamma-butyrolactone, are hydrogenated in the vapor phase to glycols over a copper chromite catalyst.

10 Claims, 1 Drawing Figure

VAPOR PRESSURE OF BUTYROLACTONE AND BUTANEDIOL

G  BUTYROLACTONE VAPOR PRESSURE
B  BUTANEDIOL VAPOR PRESSURE

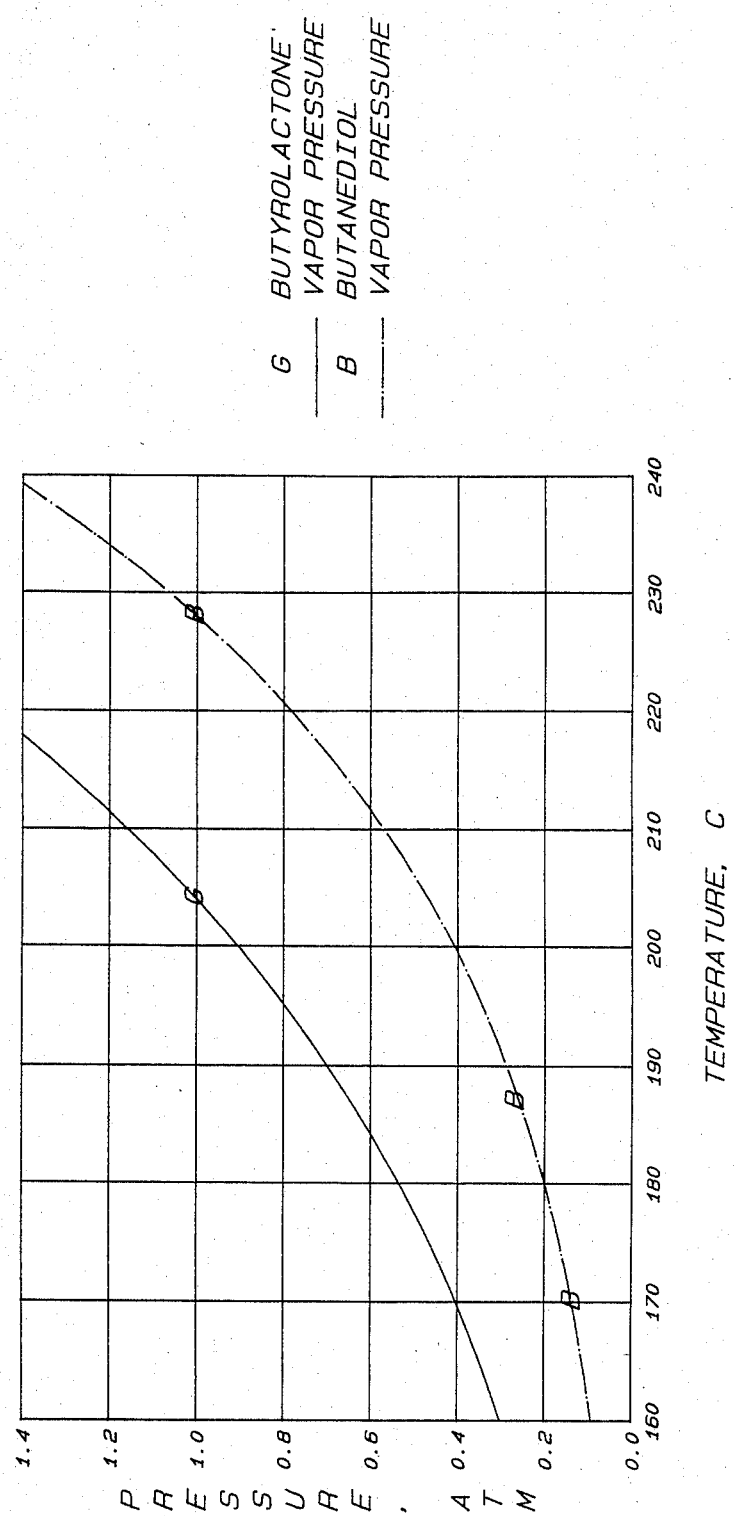

HYDROGENATION OF LACTONES TO GLYCOLS

The present invention relates to the hydrogenation of lactones to glycols. More specifically, the present invention relates to the vapor phase hydrogenation of lactones, for example, gamma-butyrolactone to glycol, for example, 1,4-butanediol, over a copper chromite catalyst.

BACKGROUND OF THE INVENTION

Methods for the production of glycols, i.e. terminally substituted aliphatic diols, are known to the art. Among desired glycols are those having four or more carbon atoms such as 1,6-hexanediol and especially, 1,4-butanediol.

1,4-butanediol and 1,6-hexanediol are useful as monomers in a number of polymers including, thermoplastics such as the polyester thermoplastics and polyether thermoplastics. Particular such thermoplastics are poly(1,4-butylene terephthalate) resin block copolymers containing blocks of poly(butyl ether) and aliphatic polyesters such as poly(hexylene adipate).

Particularly, 1,4-butanediol may be produced in a number of processes. The most commonly used process involves reacting acetylene and formaldehyde by the REPPE reaction to give but-2-yne-1,4-diol which is hydrogenated to form 1,4-butanediol. Another method, reacts allyl alcohol, produced from propylene, with i-butylene to form allyl t-butyl ether which is hydroformylated over a rhodium complex catalyst to give 4-t-butoxybutyraldehyde. This compound is then hydrogenated and cleaved under mild conditions over an acid catalyst to give 1,4-butanediol.

More pertinent to the present invention, there have also been a number of proposals to produce 1,4-butanediol in a single hydrogenation step from a diester of maleic acid or in a two step process converting maleic anhydride first to gamma-butyrolactone and subsequently in a second reaction step to 1,4-butanediol. Several references have dealt with the conversion of gamma-butyrolactone to 1,4-butanediol. The majority of such references recommend the liquid phase for carrying out the reaction. However, it is known to conduct the reaction in the vapor phase as well.

WO No. 82/03854, Bradley, et al., discloses the hydrogenolysis of gamma-butyrolactone in the vapor phase over a copper oxide and zinc oxide catalyst. Reactor productivity is generally low.

British Pat. No. 1,230,276 discloses the hydrogenation of gamma-butyrolactone using a copper oxide-chromium oxide catalyst. The hydrogenation is carried out in the liquid phase. Batch reactions are exemplified having very high total reactor pressures. Reactant and product partial pressures in the reactors are well above the respective dew points.

British Pat. No. 1,314,126 discloses the hydrogenation of gamma-butyrolactone in the liquid phase over a nickel-cobalt-thorium oxide catalyst. Batch reactions are exemplified having high total pressures and component partial pressures well above respective component dew points.

British Pat. No. 1,344,557 discloses the hydrogenation of gamma-butyrolactone in the liquid phase over a copper oxide-chromium oxide catalyst. A vapor phase or vapor containing mixed phase is indicated as suitable in some instances. A continuous flow tubular reactor is exemplified using high total reactor pressures.

British Pat. No. 1,512,751 discloses the hydrogenation of gamma-butyrolactone to 1,4-butane diol in the liquid phase over a copper oxide-chromium oxide catalyst. Batch reactions are exemplified with high total reactor pressures and, where determinable, reactant and product partial pressures well above the respective dew points.

U.S. Pat. No. 4,301,077 discloses the hydrogenation to 1,4-butanediol of gamma-butyrolactone over a Ru-Ni-Co-Zn catalyst. As taught, the reaction may be conducted in the liquid or gas phase or in a mixed liquid-gas phase. Exemplified are continuous flow liquid phase reactions at high total reactor pressures and relatively low reactor productivities.

U.S. Pat. No. 4,048,196 discloses the production of 1,4-butanediol by the liquid phase hydrogenation of gamma-butyrolactone over a copper oxide-zinc oxide catalyst. Exemplified is a continuous flow tubular reactor operating at high total reactor pressures and high reactant and product partial pressures.

The process of the above references are convenient to produce laboratory quantities of 1,4-butanediol. However, on scale-up, it is discovered that generally low reactor productivities necessitate large reactors to produce commercial quantities. Such large reactors are impractical using the high pressures of the prior art references.

Therefore, it is an object of the present invention to produce glycols from lactones, and in particular, 1,4-butanediol from gamma-butyrolactone.

It is another object of the present invention to increase reactor productivity in the hydrogenation of lactones to diols.

It is another object of the present invention to lower overall reactor pressure during such hydrogenation while increasing reactor productivity.

DETAILED DESCRIPTION OF THE INVENTION

Briefly, according to the present invention, glycols may be produced from lactones in a process comprising the steps performed consecutively or simultaneously of:

(a) contacting reactants comprising lactone and hydrogen with a copper chromite catalyst at a mass velocity of from about 1500 to about 15000 lb/hr-ft$^2$;

(b) controlling temperature and partial pressure of reactants and products to maintain said reactants and products in the vapor phase; and (c) withdrawing reactants and products at about the rate of reactant input.

Lactones intended for the method of the present invention are lactones represented by the formula:

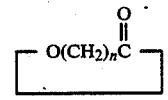

wherein n is an integer of from 3 to 10. Lactones included by the above formula include gamma-butyrolactone, delta-valerolactone, epsilon-caprolactone, etc.

Lactones used herein can be easily and cheaply obtained in commercial quantities by well-known processes. One such process, produces gamma-butyrolactone by high pressure hydrogenation of maleic anhydride in the presence of a nickel or cobalt molybdite catalyst. Another such process produces gamma-butyrolactone by treating the anhydrides or esters of 1,4-butane dicarboxylic acids or 1,4-butene dicarboxylic acids in the vapor phase with gaseous hydrogen in contact with a catalyst. This latter process is described in U.S. Pat. No. 3,065,243 which is incorporated herein by reference.

The catalyst employed in the process of this invention is reduced copper oxide-chromium oxide (also frequently referred to as copper chromite) in which the ratio by weight of copper oxide (CuO) to chromium oxide ($Cr_2O_3$) prior to reduction, is less than 10:1 and more than 2:3 but preferable less than 5:1 and more than 0.9:1. Such catalyst may also contain a stabilizer, such as calcium oxide or magnesium oxide but preferably the stabilizer is barium oxide. The catalyst may be in the form of pellets, pellet particles, and may be deposited on a support such as alumina as is well-known. Commercial tablet-shaped copper chromite catalysts contain, for example, about 33% by weight CuO, and about 38% by weight $Cr_2O_3$ and about 8% by weight BaO; or, for example, 37% by weight CuO and 52% by weight of $Cr_2O_3$. Furthermore, monomelts of silicon dioxide, aluminum oxide, alkali metal oxides or alkaline earth metal oxides may also be present. The surface area of such catalysts typically range from about 10 to about 100 $m^2/g$ and the pore volume ranges from about 0.1 to about 0.4 $cm^3/g$. Before use, these catalyst can be washed with virtually ion-free water, such as, for example, condensed steam, in order to remove all water-soluble constituents. It is highly preferred that such water-soluble constituents be removed. Further, it is advantageous to dry these catalysts, e.g., in a hydrogenation apparatus, and reduce them at about 130° to about 260° C., and from about 1 to about 300 atm pressure, in a stream of hydrogen optionally mixed with nitrogen, before they are subjected to the reaction mixture. The reduction conditions are generally maintained from about 2 to about 36 hours. Of course, the reduction can be performed under differing conditions over the reduction time.

The described catalysts are well-known to the art and generally disclosed by Homer Adkins in the book "Reactions of Hydrogen with Organic Compounds Over Chromium Oxide and Nickel Catalysts" University of Wisconsin Press, 1944, pages 12-14. The particular catalyst employed in the present invention is manufactured by Harshaw Chemical Co. under the designation "CU-1186-T1/8".

The hydrogenation of the present invention is carried out in a continuous flow reactor controlling temperature, total pressure, reactant and product partial pressure, and reactant feed rates within certain bounds. The continuous flow reactor may be a stirred tank reactor but preferably a plug flow reactor is employed. Fluid-bed reactors may be employed as appropriate, however, what with the availability of copper chromite catalysts having longer active lifetimes and operating techniques available to extend such lifetimes, the operating simplicity of fixed-bed reactors is preferred. The reactor is sized according to the skill of the art depending upon predicted reactor productivity and desired output.

Fixed-bed reactors are packed so as to force contact between, in this case, the gaseous reactants and the active catalyst. At some point along the length of a plug flow reactor, the entire cross-sectional area of the reactor should be packed with a porous catalyst in order to insure that no gas passes without catalyst contact. In the present invention, the catalyst, i.e. copper chromite catalyst, is generally packed in a fixed-bed reactor with packing density from about 90 $lb/ft^3$ to about 150 $lb/ft^3$. This packing density range is intended to cover packing densities normally employed with this catalyst.

Methods of controlling reactor temperature, total pressure, and reactant and product partial pressures are well-known to those skilled in the art. The control scheme and the hardware employed for controlling such are not critical. Temperature may be controlled using steam heating means or other means as appropriate. Though the present reaction is only slightly exothermic, such heat of reaction must be considered in controlling reactor temperature. Reactor pressure and reactant and product partial pressures may be controlled by varying the rate of withdrawing reactants and products, varying the rate of reactant input, or by a combination of a forgoing. The control of temperature, pressure, and component partial pressure, is well within the skill of the art.

In the practice of the present invention, Applicant has discovered that the hydrogenation of lactone to glycol can be carried out with higher reactor productivities than heretofore thought possible. Applicant has identified certain reactor conditions necessary to achieve such productivities. Reactor temperature may vary from about 160° C. to about 230° C. and may of course be non-isothermal. Over this temperature range, and at all points within the reactor all significant reactants and significant reaction products must be maintained in the vapor phase. FIG. 1 shows a pressure/temperature diagram of the significant reactants and products for the hydrogenation of gamma-butyrolactone over this temperature range. In order to maintain the vapor phase of the reactants and products at any temperature, the partial pressure of each such reactant and product should be maintained in the reactor for the entire portion of residence time below respective dew points as shown in FIG. 1. Thus, for example, if the reactor is isothermal at 210° C. or nonisothermal with a minimum temperature of 210° C. then the partial pressure of 1,4-butanediol, a product, should not exceed about 0.55 atmospheres at any point in the isothermal reactor or at the point of minimum temperature in the non-isothermal reactor. Applicants have further found that temperature should be as low as possible, preferably between 170 and 200° C. so long as the least volatile reactant or product is maintained in the vapor phase. It is most preferred that the partial pressure of each reactant and product is as high as possible so long as each reactant or product is maintained in the vapor phase. Of course, while it is desirable to control all reactant and product partial pressures as close to the dew point as possible, it is generally difficult to control the partial pressure of a reactant independent of products and conversely. Thus, the partial pressures of the reactants and products is generally controlled based on the partial pressure of the least volatile compound in the reaction chain. As a practical matter, it is the partial pressure of this least volatile reactant or product which will determine maximum partial pressures for all other reactants or products. Generally, in the present invention, the least volatile reactant or product is the glycol product, i.e. 1,4-butanediol. Its maximum vapor pressure should fall within 0.30 and preferably 0.15 atmospheres of its dew point at any point in the reactor. Total reactor pressure, that is, the sum of the partial pressures of the reactants and products plus hydrogen pressure should range from about 5 to about 75 atmospheres, but preferably less than 50 atmospheres.

Using the above catalysts and conditions, it is surprisingly found that high mass velocities may be employed with excellent conversions, selectivities, and thus heretofore unachieved reactor productivities. Functional reactant mass velocities under the above conditions range from about 1,500 to about 15,000 lb/hr-ft$^2$ and preferably from about 2,000 to about 10,000 lb/hr-ft$^2$.

Of course, it is obvious to those skilled in the art that few of the above variables are independent. It is difficult to control 1,4-butanediol partial pressure independent of gamma-butyrolactone feed rate and degree of conversion. However, those skilled in the art have it within their knowledge to control the conditions of the reactor within the above described bounds. The practice of this invention will be still further apparent by the following illustrative examples.

EXAMPLE 1

Copper chromite pellets having the designation "CU-1186-T1/8 " obtained from Harshaw Chemical Company and having a ratio by weight CuO:Cr$_2$O$_3$:BaO of 42:44:9 were reduced according to the following procedure: About 7.8 lb. of the pellets were charged to a jacketed, steel reactor tube included in a hermetically-joined system comprising a recycle compressor, flowmeter, preheater, reactor tube, condenser, and product tank. The height/diameter ratio of the catalyst bed was approximately 115. The entire system was thoroughly flushed with nitrogen to purge it of any oxygen. The system was then pressurized with nitrogen and valves adjusted to obtain a flow of about 57 liters of the gas per minute at a reactor inlet pressure of about 8 pounds per square inch. The preheater and reactor jacket temperature were adjusted to obtain a gas temperature of about 130° C. in the catalyst bed. Hydrogen was then fed into the circulating nitrogen stream at a rate of about 1 liter per minute. These conditions were held for about 2 hr, then the hydrogen rate was increased to 2 liters/min and held for 8 hr. The hydrogen rate was increased to 4.5 liters/min and held about 2 hr; then increased to 9 liters/min and held 2 hr. The nitrogen rate was then decreased to 25 liters/min and the hydrogen increased to 25 liters/min, and over the next 3.5 hours the catalyst bed temperature was increased to 170° C. The nitrogen was then turned off and the system thoroughly flushed with hydrogen to remove residual nitrogen.

After reduction of the catalyst as described above, the compressors were turned on and set so that the hydrogen flow rate was 17.1 lbs/hour. The system pressure was set to 600 psig and the vaporizer and reactor temperatures set to 210° C. Butyrolactone was then fed to the vaporizer at a rate of 4.8 lbs/hour. The gases produced by this vaporization were then passed through the reduced above-mentioned catalyst bed which was maintained at a temperature of about 210° C. The mass velocity of the stream through the catalyst bed was 1847 lb/hr-ft$^2$.

The resulting product vapors were condensed to give a mixed condensate comprising butyrolactone (GBL), 1,4-butanediol (DIOL), tetrahydrofuran (THF), butanol (BUOH), and water. The condensate obtained was analyzed by gas-liquid chromatography, and it was found that 31.1 parts of butyrolactone and 64.5 parts of butanediol were produced per 100 parts of butyrolactone fed. This corresponds to 68.4% conversion of the butyrolactone and 92.3% selectivity to butanediol.

EXAMPLE 2

The operating procedure of Example 1 was repeated under the conditions shown in Table 1. These conditions were repeated 5 times over a period of 380 actual operating hours. The results are given in Table 1. Substantially the same conversions and yields were obtained and at the end of this period there was no indication of catalyst inactivation.

EXAMPLES 3-4

The operating procedure of Example 1 was repeated under the conditions shown in Table 1. The results are given in Table 1.

TABLE 1

| EX | REACTR PRESS (PSIG) | REACTR TEMP (°C.) | H$_2$ RECYCLE + FEED (LB/HR) | GBL FEED (LB/HR) | H$_2$/GBL MOLE RATIO | PRODUCT MOLE % | | | |
|---|---|---|---|---|---|---|---|---|---|
| | | | | | | THF | BUOH | GBL | DIOL |
| 1 | 600 | 210.9 | 9.84 | 4.82 | 88 | 3.5 | 0.5 | 31.1 | 64.5 |
| 2.0 | 600 | 209.9 | 17.16 | 7.85 | 94 | 2.3 | 0.3 | 33.2 | 63.9 |
| 2.1 | 600 | 209.9 | 17.10 | 8.12 | 91 | 1.9 | 0.4 | 33.1 | 64.3 |
| 2.2 | 600 | 213.5 | 17.00 | 8.21 | 89 | 2.2 | 0.4 | 35.1 | 61.9 |
| 2.3 | 600 | 211.0 | 17.00 | 8.40 | 87 | 1.9 | 0.4 | 34.5 | 62.9 |
| 2.4 | 600 | 210.3 | 17.10 | 8.60 | 86 | 1.7 | 0.4 | 33.5 | 63.8 |
| 2.5 | 600 | 209.4 | 17.10 | 7.60 | 97 | 1.9 | 0.4 | 32.8 | 64.5 |
| 3 | 600 | 211.0 | 25.60 | 12.00 | 92 | 1.3 | 0.3 | 36.8 | 61.4 |
| 4 | 600 | 209.3 | 32.60 | 16.10 | 87 | 1.0 | 0.2 | 39.6 | 58.8 |

| GBL CONV % | DIOL SEL % | REACTR PROD (G-MOL/L-HR) | INLET GBL MASS VEL$_2$ (LB/FT-HR) | OUTLET DIOL VAP PRESS (ATM) |
|---|---|---|---|---|
| 68.4 | 92.3 | 6.80 | 1847 | .30 |
| 66.0 | 94.6 | 10.94 | 3151 | .28 |
| 66.1 | 95.1 | 11.40 | 3177 | .29 |
| 64.2 | 94.4 | 11.11 | 3176 | .28 |
| 64.7 | 95.0 | 11.53 | 3200 | .29 |
| 65.8 | 95.0 | 12.00 | 3238 | .30 |
| 66.4 | 95.3 | 10.74 | 3112 | .27 |
| 62.4 | 96.3 | 16.10 | 4737 | .28 |
| 59.4 | 96.9 | 20.69 | 6135 | .27 |

EXAMPLES 5 to 9

Copper chromite pellets having the designation "CU-0203-T1/8" obtained from Harshaw Chemical Company and having a ratio by weight of CuO:Cr2O3 of 79:17 were reduced according to a procedure similar to that given in Example 1. About 13 lbs of the pellets were used. The operating procedure of Example 1 was repeated under the conditions shown in Table 2. The results were given in Table 2.

TABLE 2

| EX | REACTR PRESS (PSIG) | REACTR TEMP (°C.) | H₂ RECYCLE + FEED (LB/HR) | GBL FEED (LB/HR) | H₂/GBL MOLE RATIO | PRODUCT MOLE % | | | |
|---|---|---|---|---|---|---|---|---|---|
| | | | | | | THF | BUOH | GBL | DIOL |
| 5 | 600 | 211 | 6.2 | 2.97 | 89 | 5.5 | 1.1 | 31.8 | 60.4 |
| 6 | 600 | 211 | 8.6 | 4.26 | 86 | 4.4 | 0.8 | 32.7 | 61.9 |
| 7 | 600 | 211 | 12.2 | 6.14 | 85 | 3.0 | 0.6 | 32.9 | 63.4 |
| 8 | 600 | 212 | 17.1 | 7.98 | 92 | 2.3 | 0.4 | 33.1 | 63.6 |
| 8.1 | 600 | 213 | 17.1 | 8.22 | 89 | 2.4 | 0.4 | 35.2 | 61.9 |
| 8.2 | 600 | 209 | 17.1 | 8.27 | 88 | 2.2 | 0.4 | 33.0 | 64.2 |
| 8.3 | 600 | 210 | 17.1 | 8.30 | 88 | 2.2 | 0.3 | 32.2 | 64.3 |
| 8.4 | 600 | 211 | 17.1 | 8.48 | 86 | 2.3 | 0.4 | 33.0 | 64.0 |
| 9 | 600 | 212 | 32.1 | 16.3 | 84 | 1.2 | 0.2 | 32.6 | 65.7 |

| GBL CONV % | DIOL SEL % | REACTR PROD (G-MOL/L-HR) | INLET GBL MASS VEL (LB/FT²-HR) | OUTLET DIOL VAP PRESS (ATM) |
|---|---|---|---|---|
| 67.4 | 87.0 | 2.98 | 1155 | 0.27 |
| 66.7 | 89.9 | 4.37 | 1620 | 0.29 |
| 66.2 | 93.2 | 6.49 | 2311 | 0.30 |
| 66.1 | 94.1 | 8.50 | 3160 | 0.29 |
| 64.0 | 94.7 | 8.53 | 3190 | 0.28 |
| 66.0 | 95.0 | 8.88 | 3196 | 0.30 |
| 67.0 | 94.1 | 8.96 | 3200 | 0.30 |
| 66.2 | 94.6 | 9.09 | 3223 | 0.31 |
| 66.5 | 97.0 | 18.00 | 6110 | 0.32 |

COMPARATIVE DATA

The following Table 3 compiles comparative data from various references teaching the production of butanediol from gamma-butyrolactone.

TABLE 3

| | | EX | REACTR PRESS (PSIG) | REACTR TEMP (°C.) | H₂ RECYCLE + FEED (G/HR) | GBL FEED (G/HR) | H₂/GBL MOLE RATIO |
|---|---|---|---|---|---|---|---|
| G82116552A | Cu—Zn | 22 | 410 | 226 | 13.9 | 16.4 | 36.5 |
| | | 23 | 220 | 215 | 40.2 | 16.6 | 106 |
| | | 24 | 405 | 217 | 40.2 | 15.6 | 111 |
| US 4301077 | Ru—Ni—Co—Zn | 1 | 1000 | 220 | 3.5 | 13.5 | 11.1 |
| US 4048196 | Cu—Zn | 1 | 3750 | 180 | — | — | — |

| PRODUCT MOLE % | | | | GBL CONV % | DIOL SEL % | REACTR PROD (G-MO/L-HR) | OUTLET DIOL VAP PRESS (ATM) |
|---|---|---|---|---|---|---|---|
| THF | BUOH | GBL | DIOL | | | | |
| 12.40 | 1.20 | 66.8 | 12.2 | 47.6 | 41.8 | 2.80 | 0.09 |
| 0.02 | 0.03 | 90.6 | 9.2 | 9.4 | 97.4 | 0.55 | 0.01 |
| 0.04 | 0.04 | 84.0 | 15.8 | 16.1 | 98.4 | 2.10 | 0.04 |
| — | 1.00 | 52.4 | 39.7 | 47.6 | 83.4 | 1.70 | LIQ |
| — | — | — | — | — | — | 10.00 | LIQ |

What is claimed is:

1. A process for the production of glycol comprising the steps performed consecutively of simultaneously of:
   (a) contacting reactants comprising lactone and hydrogen with a copper chromite catalyst at temperatures within the range of about 160° to about 230° C. and a mass velocity of from about 1500 to about 15000 lb/hr-ft²;
   (b) controlling temperature and partial pressures of reactants and proucts to maintain said reactants and products in the vapor phase; and
   (c) withdrawing reactants and products at about the rate of reactant input.

2. The process of claim 1 wherein said lactone is gamma-butyrolactone and said glycol is 1,4-butanediol.

3. The process of claim 2 wherein said lactone is epsilon-caprolactone and said glycol is 1,6-hexanediol.

4. The process of claim 1 wherein the maximum partial pressure of the least volatile reactants and products is controlled within about 0.30 atmospheres of its dew point.

5. The process of claim 2 wherein the maximum partial pressure of 1,4-butanediol is controlled within about 0.30 atmospheres of its dew point.

6. The process of claim 1 wherein said reactants are contacted with said copper chromite catalyst at a mass velocity of from about 2000 to about 10000 lb/hr-ft².

7. The process of claim 1 wherein said partial pressure of said reactants and products is controlled by varying the rate of withdrawing reactants and products.

8. The process of claim 1 wherein the partial pressure of said reactants and products is controlled by varying the rate of input of said reactants.

9. The process of claim 1 wherein temperature ranges from about 180° C. to about 200° C.

10. The process of claim 1 wherein total reactor pressure ranges from about 5 to about 75 atmospheres.

* * * * *